US010925991B2

(12) United States Patent
Van Sleeuwen et al.

(10) Patent No.: US 10,925,991 B2
(45) Date of Patent: Feb. 23, 2021

(54) AIR FRESHENER GEL CONTAINING CELLULOSE, HEMICELLULOSE, LIGNIN

(71) Applicant: Firmenich SA, Geneva (CH)

(72) Inventors: Rutger Van Sleeuwen, Plainsboro, NJ (US); Anaick Nicolae, Cruseilles (FR); Gerald Allison, Plainsboro, NJ (US); Valery Normand, Plainsboro, NJ (US)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 15/736,875

(22) PCT Filed: Jul. 29, 2016

(86) PCT No.: PCT/EP2016/068150
§ 371 (c)(1),
(2) Date: Dec. 15, 2017

(87) PCT Pub. No.: WO2017/017251
PCT Pub. Date: Feb. 2, 2017

(65) Prior Publication Data
US 2019/0070327 A1  Mar. 7, 2019

Related U.S. Application Data

(60) Provisional application No. 62/198,168, filed on Jul. 29, 2015.

(30) Foreign Application Priority Data

Sep. 7, 2015  (EP) ..................................... 15184080

(51) Int. Cl.
*A61L 9/012*  (2006.01)
*A61L 9/04*  (2006.01)

(52) U.S. Cl.
CPC ............... *A61L 9/012* (2013.01); *A61L 9/048* (2013.01); *A61L 2209/21* (2013.01)

(58) Field of Classification Search
None
See application file for complete search history.

(56) References Cited

U.S. PATENT DOCUMENTS

| 6,602,994 B1 * | 8/2003 | Cash ...................... A61K 8/027 536/100 |
| 7,833,558 B2 | 11/2010 | Larsen et al. |
| 2005/0037080 A1 * | 2/2005 | Lynch ................. A01M 1/2055 424/488 |
| 2007/0031572 A1 | 2/2007 | Larsen et al. |

FOREIGN PATENT DOCUMENTS

| EP | 1078008 B1 | 10/2012 |
| LT | 11751 B | 6/1997 |

OTHER PUBLICATIONS

International Search Report and Written Opinion for International Application No. PCT/EP2016/068150, dated Oct. 28, 2016.

* cited by examiner

*Primary Examiner* — Robert A Wax
*Assistant Examiner* — Quanglong N Truong
(74) *Attorney, Agent, or Firm* — Paul Zagar

(57) ABSTRACT

The present invention relates to the field of air freshener. It relates more particularly to a gel composition which allows for an effective and prolonged evaporation of an active volatile ingredient contained therein. The gel device of the present invention comprises an active volatile ingredient and a gelling agent essentially formed of cellulose, hemicellulose and pectin.

11 Claims, 1 Drawing Sheet

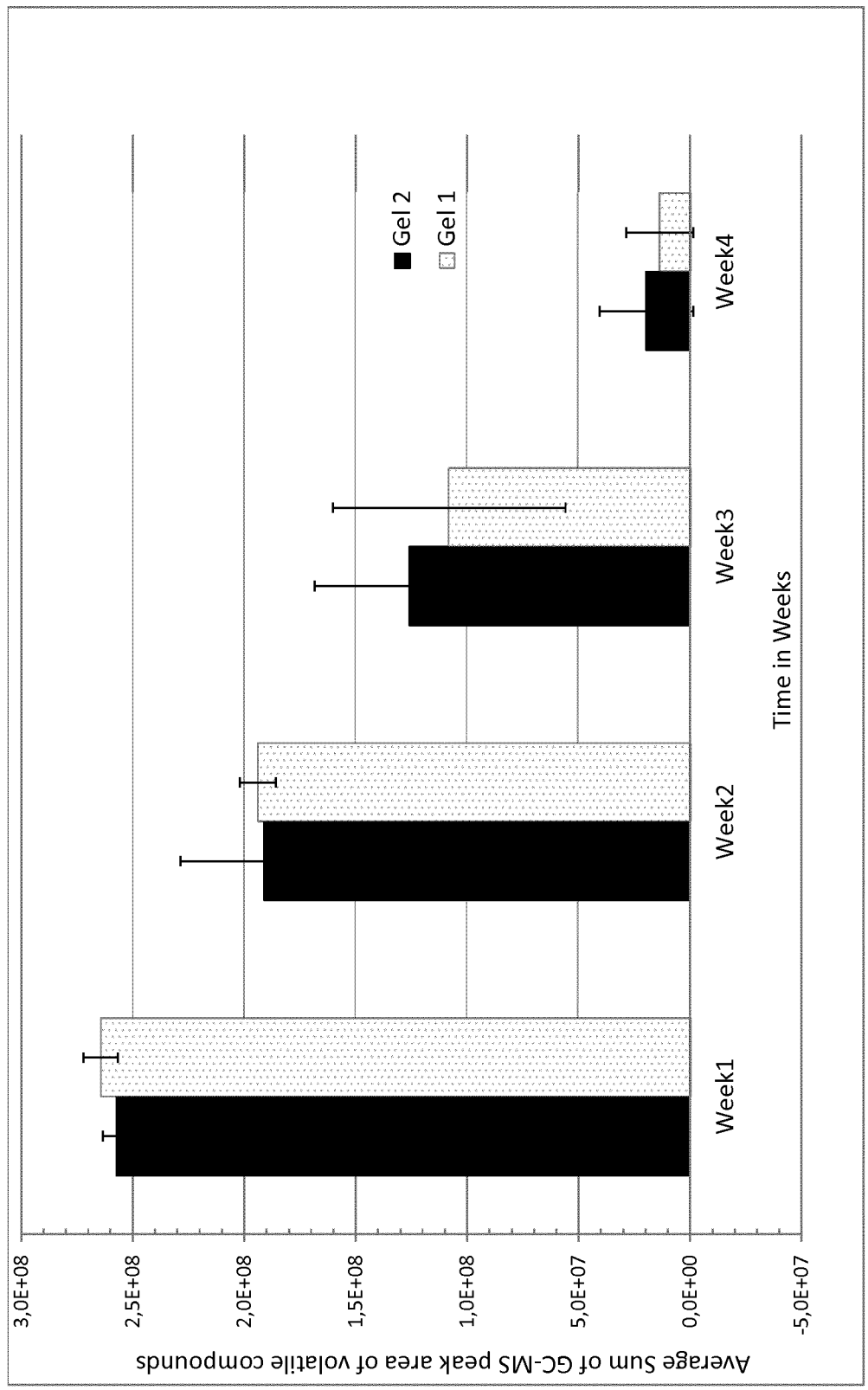

AIR FRESHENER GEL CONTAINING CELLULOSE, HEMICELLULOSE, LIGNIN

RELATED APPLICATIONS

This application is a national stage application under 35 U.S.C. § 371 filing of International Patent Application PCT/EP2016/068150, filed Jul. 29, 2016, which claims the benefit of U.S. Provisional Application No. 62/198,168, filed Jul. 29, 2015 and EP Application 15184080.8, filed Sep. 7, 2015. The contents of which are incorporated herein by reference in their entirety.

TECHNICAL FIELD

The present invention relates to the field of air fresheners. It relates more particularly to a gel composition which allows for an effective and prolonged evaporation of an active volatile ingredient contained therein such as a perfume. The gel composition of the present invention comprises an active volatile ingredient and a gelling agent comprising cellulose, hemicellulose and pectin.

PRIOR ART

The use of various devices for the diffusion of volatile compounds, for example perfumes, sanitizing agents, insect repellents and the like, has become more and more current in recent years. Air-freshening devices or deodorizers are currently used in practically all households to mask bad odors or to diffuse fragrances or other volatile active ingredients to the air surrounding the device, in particular in rooms and cupboards, litter containers, and other closed environments.

Amongst the various types of devices that can be used to diffuse fragrances and other air modifying substances such as purifying or sanitizing agents, one class of systems capable of diffusing active volatile ingredients are solid state devices consisting of solid materials or carriers impregnated with an active ingredient. Such devices may be formed of various materials which are capable of absorbing the active ingredient and subsequently releasing it in a more or less controlled manner. Examples of such known materials include gels, such as agar-agar or sodium stearate gels, synthetic polymer resins, or blocks of mineral material, e.g. plaster or silica.

Devices based on gels, also known as hydrogels, are well known in the art. Gel compositions usually comprise water, a gelling agent and volatile compounds wherein the gelling agent is an absorbing material selected from the so-called superabsorbent polymers such as starch based systems, chemically modified cellulose or natural gums.

An example of gel composition useful as an air freshener reported in US20050037080 comprises alginate as a gel-forming polymer, an added-polymer such as carboxymethyl cellulose, a divalent cation and an active substance such as perfume. However, said gel composition requires the presence of non-naturally-occurring ingredient such as carboxymethyl cellulose.

One of the commonly used gel compositions is based on natural carrageenans as gelling agents. While this type of hydrogel gives satisfaction in terms of active ingredients releasing profile over time, it however suffers from instability when exposed to high heat and possesses off-notes which requires the use of high amounts of perfume and so increases the cost of this composition.

Therefore, there is a need to provide a gel composition comprising a natural gelling agent capable of diffusing volatile compounds over a long period of time as carrageenan while overcoming drawbacks of prior art solutions such as off-notes.

The present invention provides a solution to the above mentioned problems by using a gel composition comprising cellulose, hemicellulose and pectin. U.S. Pat. No. 7,833,558 describes a method to prepare a fiber-containing pectin product, and mention gelling and viscous giving properties. However the gel composition of the present invention which is an air freshener is not described or suggested in any prior art document.

SUMMARY OF THE INVENTION

The invention relates to a novel gel composition which demonstrates excellent release over time of volatile active ingredients included therein which shows less off-notes and improved heat stability compared to commercially relevant gels based on carrageenans. In particular, said gel composition comprising cellulose, hemicellulose and pectin as gelling agent provides an advantageous air freshener with a good fragrance intensity profile and lower off-notes.

A first object of the present invention is therefore a gel composition comprising:
  a) a gelling agent comprising cellulose, hemicellulose and pectin, in an amount comprised between 0.1% and 10% by weight, relative to the total weight of the composition;
  b) an active volatile ingredient-containing oil in an amount comprised between 0.1% and 5% by weight, relative to the total weight of the composition;
  c) water in an amount comprised between 85% and 98.9% by weight, relative to the total weight of the composition;
  d) a bivalent cation, in an amount comprised between 0.01% and 1% by weight, relative to the total weight of the composition;
  e) a sequestering agent, in an amount below 0.5% by weight, relative to the total weight of the gel composition; and
  f) a pH modifier, in an amount below 3% by weight, relative to the total weight of the gel composition;
  wherein that said composition is an air freshener.

A second object of the present invention is a process for the preparation of a gel composition as defined above comprising the following steps:
  a) mixing a gelling agent comprising cellulose, hemicellulose and pectin with water;
  b) adding to the mixture obtained in step a) a sequestering agent;
  c) optionally heating the mixture obtained in step b);
  d) adding to the mixture obtained in step c):
    i) a bivalent cation;
    ii) a pH modifier; and
    iii) an active volatile ingredient containing-oil.

A third object of the present invention consists of a method to modulate, enhance or modify the evaporation of an active volatile ingredient comprising the step of providing a gel composition as defined above.

A last object of the present invention the use of the gel composition as defined above as an air freshener.

BRIEF DESCRIPTION OF THE DRAWINGS

FIG. 1: Represents the fragrance abundance in the surrounding environment measured by headspace analysis of a perfume released from a composition according to the invention at different moments in time.

DESCRIPTION OF THE INVENTION

The gel composition of the present invention-maintains the advantage of the commercial carrageenan-based gel, i.e. slow release of perfume and nature-friendly gel, while boosting the perfume intensity initially perceived. Moreover, the gel composition of the invention avoids marine off-notes typical of carragenenan-based gel composition. The invention therefore allows providing an efficient air freshener with a reduced concentration of the active volatile ingredient-containing oil, thus reducing advantageously the cost of the gelling composition.

Therefore, a first object of the present invention is a gel composition comprising:
a) a gelling agent comprising cellulose, hemicellulose and pectin, in an amount comprised between 0.1% and 10% by weight, relative to the total weight of the composition;
b) an active volatile ingredient-containing oil in an amount comprised between 0.1% and 5% by weight, relative to the total weight of the composition;
c) water in an amount comprised between 85% and 98.9% by weight, relative to the total weight of the composition;
d) a bivalent cation, in an amount comprised between 0.01% and 1% by weight, relative to the total weight of the composition;
e) a sequestering agent, in an amount below 0.5% by weight, relative to the total weight of the gel composition; and
f) a pH modifier, in an amount below 3% by weight, relative to the total weight of the gel composition;
wherein that said composition is an air freshener.

The gelling agent of the gel composition of the present invention comprises cellulose, hemicellulose and pectin, such as that sold under the trade name FiberGel® (trademark from Florida Food Products, Inc. and commercially available from Florida Food Products, Inc.) or CitriFi® (trademark from Fiberstar® and commercially available from Fiberstar®). Preferably, the gelling agent is devoid of chemically modified cellulose. More preferably the gelling agent comprises only naturally-occurring compounds. Preferably, the gelling agent of the gel of the present invention comprises cellulose, hemicellulose, pectin such as that sold under the trade name FiberGel®. Said gelling agent is used in an amount comprised between 0.1% and 10% by weight, relative to the total weight of the composition, preferably, in an amount comprised between 1% and 5%, even more preferably, in an amount comprised between 2% and 3%. Preferably, the gelling agent comprises cellulose in an amount comprised between 5 and 25 wt %, relative to the total weight of the gelling agent, hemicellulose in an amount comprised between 5 and 25 wt %, relative to the total weight of the gelling agent and in an amount comprised between 25 and 60 wt %, relative to the total weight of the gelling agent.

The composition of the invention further comprises an active-volatile ingredient-containing oil in an amount comprised between 0.1% and 5% by weight, relative to the total weight of the composition. By "active volatile ingredient" it is meant here an individual ingredient, or a mixture of ingredients capable of imparting perceptible and desirable benefits to the quality of the air into which they are diffused. The active volatile ingredient is preferably selected from the group consisting of a perfume, a perfume ingredient, a malodor counteractant, a bactericide, insect control agents, biocide actives and mixture thereof. Preferably, the active volatile ingredient is a perfume or a malodor counteractant. Even more preferably, the active volatile ingredient is a perfume.

As "perfume" one may use any perfuming ingredient or a mixture thereof. A "perfuming ingredient" is meant here as a compound which is of current use in the perfumery industry, i.e. a compound which is used as active ingredient in perfuming compositions or in perfumed products in order to impart a hedonic effect into its surroundings. In other words, such an ingredient or mixture, to be considered as being a perfuming one, must be recognized by a person skilled in the art of perfumery as being able to impart or modify, preferably in a positive or pleasant way, the odor of a composition or product, and not just as having an odor. Moreover, this definition is also meant to include compounds that do not necessarily have an odor but are capable of modulating the odor of a perfuming composition or of a perfumed product and, as a result, of modifying the perception by a user of the odor of such a composition or product.

The nature and type of these perfuming ingredients do not warrant a more detailed description here, which in any case would not be exhaustive, the skilled person being able to select them on the basis of his general knowledge, the intended use or application and the desired organoleptic effect. In general terms, these perfuming ingredients belong to chemical classes as varied as alcohols, aldehydes, ketones, esters, ethers, acetates, nitriles, terpene hydrocarbons, nitrogenous or sulphurous heterocyclic compounds and essential oils. Said perfuming ingredients can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds. According to a particular embodiment, the perfume introduced into the gel composition of the present invention imparts a floral/fruity organoleptic note.

Typically, the perfume may also contain a carrier of current use in perfumery such as a solvent. The amount and nature of such current perfume additives can be selected and its amount adjusted by the skilled person so as to not adversely affect the properties of the gel according to the invention. Perfume ingredients or mixtures of ingredients may also be carried in an encapsulated form, enclosed in encapsulating carriers of current use in perfumery. Fragrance microcapsules may be advantageous to protect particularly fragile perfuming ingredients, or yet to delay the release of certain perfume components and thus create a slow release impact. The same applies when so-called pro-fragrances (i.e. chemical substances of high molecular weight, generally not odorant as such but able to generate an odorant by chemical or photochemical reaction under use conditions) are used according to the invention.

By the term "malodor counteractant" or "malodor counteracting ingredient" we mean here compounds which are capable of reducing the perception of malodor, i.e. of an odor that is unpleasant or offensive to the human nose, by counteracting and/or masking malodors. In particular embodiments, these compounds have the ability to react with key compounds which are known or suspected to be the cause of the malodor. The reactions result in reduction of the malodor materials' airborne levels and consequent reduction in the perception of the malodor.

The active volatile ingredient may also be an insect control agent. Non-limiting examples of suitable insect control agents include birch, DEET (N,N-diethyl-m-toluamide), essential oil of the lemon *eucalyptus* (*Corymbia citriodora*) and its active compound p-menthane-3,8-diol (PMD), picaridin (hydroxyethyl isobutyl piperidine carboxylate), Nepelactone, *Citronella* oil, Neem oil, Bog Myrtle (*Myrica Gale*), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

The nature and type of the active volatile ingredients does not warrant a more detailed description here, which in any case would not be exhaustive, the skilled person being able to select them on the basis of its general knowledge and according to intended use or application.

The active volatile ingredients can be dissolved in any suitable solvent. According to a preferred embodiment of the invention, the solvent is free of VOC compounds. By "VOC" we mean here the Volatile Organic Compounds as defined by the Environmental Protection Agency, and in particular we mean $C_1$-$C_5$ alkanols, such as ethanol, or $C_1$-$C_5$ alkanediols, such as ethylene glycol.

Examples of particularly appreciated VOC free solvents are methoxylated siloxanes (for example those sold under the Dow Corning® Fluid trade-names), mineral oils and vegetable oils such as for example olive oil, castor oil and sunflower oil.

In all embodiments of the invention, the amount of active volatile ingredient or mixture of ingredients is preferably from 0.1% to 5% by weight, and more preferably from 1.0% to 2.0% by weight of active volatile ingredient, relative to the total weight of the gel.

The composition of the invention further comprises water in an amount comprised between 85% and 98.9% by weight, relative to the total weight of the composition, preferably in an amount comprised between 90% and 98.9% by weight, relative to the total weight of the composition.

The composition of the invention further comprises a bivalent cation in an amount comprised between 0.01% and 1% by weight, relative to the total weight of the composition. The bivalent cation is a calcium salt. Non limiting examples of bivalent cation are calcium phosphate and calcium chloride. According to a preferred embodiment the bivalent cation is calcium phosphate. The total amount of the bivalent cation in the gel composition shall be comprised between 0.1% and 1% by weight, relative to the total weight of the gel composition, preferably the total amount of the bivalent cation shall be comprised between 0.1% and 0.8% by weight, relative to the total weight of the gel composition, and more preferably, between 0.2% and 0.5% by weight, relative to the total weight of the gel composition.

The composition of the invention further comprises a sequestering agent. By the term "sequestering agent", it is meant the normal meaning in the art, i.e. compounds which allow releasing slowly a bivalent cation in order to obtain a rigid and uniform gel. A detailed description of the nature and type of sequestering agent commonly used in a gel composition cannot be exhaustive. Many of these ingredients are well known by the person skilled in the art and have been listed in reference text such as the book from R. S. Igoe, Dictionary of Food Ingredients, 2011, Springer, USA. However, one can cite as non-limiting examples sequestering agent such as sodium, ammonium or potassium hexaphosphate, sodium, ammonium or potassium tetraphosphate, sodium, ammonium or potassium tripolyphosphate, sodium, ammonium or potassium triphosphate, or sodium, ammonium or potassium pyrophosphate, which are the most commonly used. According to a preferred embodiment the sequestering agent is sodium tripolyphosphate. The total amount of the sequestering agent in the process of the invention shall be below 0.5% by weight, relative to the total weight of the gel composition. Preferably, the total amount of the sequestering agent in the process of the invention shall be comprised between 0.001% by weight and 0.5% by weight, relative to the total weight of the gel composition, even between 0.1% by weight and 0.3% by weight, relative to the total weight of the gel composition.

The composition of the invention further comprises a pH modifier. The pH modifier is added to lower the pH. A non-limiting examples of suitable pH modifier include Glucono delta lactone, lactic acid lactone, glycolic acid lactone and L-Lactate. Preferably, the pH modifier is glucono delta lactone Glucono delta lactone and L-Lactate. Even more preferably, the pH modifier is glucono delta lactone. The pH modifier is added in in an amount below 3% by weight, relative to the total weight of the gel composition, preferably in an amount comprised between 0.01% to 3% by weight, relative to the total weight of the gel composition.

The composition according to the invention is an air freshener. The term "air freshener" should be given its normal meaning in the art, i.e. a composition able to diffuse in its surrounding environment a volatile active ingredient such as perfume. Examples of air fresheners include but are not limited to plug ins, wax melt, candle, toilet bowl block or gel. Preferably the air freshener is a hydrogel air freshener.

The gel of the present invention may also optionally include one or more additional components so to provide enhanced or additional aesthetic and/or functional improvements thereto. In particular, the additional materials that may be included in the gel device include antibacterial agents, antimicrobial agent, preservative agent, coloring agents, decorative materials, stabilizers, antioxidants, emulsifier, surfactant and UV blockers. Stabilizers may limit the syneresis such as guar gum, carboxy methyl cellulose or Locust Bean Gum or may prevent crust formation and or plasticize such as cetyl alcohol or polyethylene glycol. Another optional but useful component is an indicator which helps the consumer assert when the active volatile ingredient is no longer present in the gel (fragrance exhausted, no longer diffused), i.e. an end point indicator.

According to a particular embodiment, the optional ingredients of the gel of the present invention may be selected from the group consisting of polyethylene glycol, dibutyl lauroyl glutamide, dibutyl ethylhexanoyl glutamide, Locust Bean Gum, $C_{14-18}$ alcohol such as Cetyl alcohol, Guar Gum, carboxy methyl cellulose and a mixture thereof.

Generally, the total amount of such optional ingredients in the gels of the invention shall not be above 10% by weight, relative to the total weight of the gel composition, more preferably below 2% by weight, relative to the total weight of the gel composition.

These optional ingredients do not warrant a more detailed description here, which would in any case not be exhaustive. The skilled person is capable of selecting them on the basis of general knowledge in the art and the desired characteristics of the gel device. In particular, the kind and amount of the additional ingredients are selected in a manner ensuring that the rigidity and other desirable properties of the gel are not affected.

According to a preferred embodiment, the gel composition of the present invention is also advantageous from an environment point of view. Indeed, as stated above, the solvent used in the invention can be VOC free. Moreover, the gelling agent is derived from plant materials and is not harmful to the environment. In particular, it is biodegradable. The gelling agent is also advantageous from a safety point of view with regard to the environment and human beings, so that it can even be used in cosmetic products.

According to any one of the above embodiments, the composition of the invention is essentially free from alginate.

According to any one of the above embodiments, the composition of the invention is essentially free from surfactant or emulsifier. In particular, the active volatile ingredient-containing oil is free of surfactant.

In another aspect, the invention provides a process for the preparation of a gel composition as defined above comprising the following steps:
 a) mixing a gelling agent comprising cellulose, hemicellulose and pectin with water;
 b) adding to the mixture obtained in step a) a sequestering agent;
 c) optionally heating the mixture obtained in step b);
 d) adding to the mixture obtained in step c):
  i) a bivalent cation;
  ii) pH modifier; and
  iii) an active volatile ingredient containing-oil.

According to a preferred embodiment, the mixture obtained in step b) is heated. The mixture obtained in step b) is heated to a temperature preferably comprised between 80° C. and 100° C., more preferably between 80° C. and 85° C.

According to a preferred embodiment, the bivalent cation is added before the pH modifier.

The addition during the process of the present invention of sequestering agent and pH modifier allows releasing slowly calcium cation in order to obtain a uniform and rigid gel.

The amount of gelling agent, active volatile ingredient, bivalent cation, sequestering agent and pH modifier are defined in previous sections of this description.

According to preferred embodiments of this process, the fluid gel obtained in step d) is poured into a mold or suitable container before being allowed to cool down to room temperature (typically 15 to 25° C.). Such embodiments make it possible to obtain solid gels with a determined form and allow the realization of decorative air fresheners and other gel devices. Of course, the gel may also be used as obtained above, without employing a mold or a container.

Any optional ingredients that may be added to the gel composition of the invention are added to the aqueous solution of the gelling agent or at any time after heating the mixture obtained in step b). The skilled person in the art is well able to add the optional ingredients at the most appropriate step of the process in function of their natures.

All embodiments of the gel composition according to the invention can be prepared according to the above-described process, wherein the use of preferred ingredients and relative proportions thereof, as defined in above, make it possible to obtain a variety of gels with advantageous properties.

Another object of the present invention is a gel composition obtainable by the process of any of the below-described embodiments.

We have found that the gel composition of the present invention advantageously provides a very uniform and prolonged diffusion of the active ingredients carried therein. Contrary to the prior known carrageenan gels, the marine off-note which lead to use a certain amount of perfume, are not perceived in the present invention.

As anticipated above, the composition of the invention can be contained in, or associated with, a consumer article, whereby as a consumer article it is intended here more specifically a volatile material dispenser. Therefore, a consumer article in the form of a volatile material dispenser containing the gel composition of the invention is also an object of the present invention. In fact, a container and an adequate composition of the invention will compose said consumer article. The composition will be housed by the container and at least a portion of the container surface is able to allow the release of the vapors of the volatile liquid component into the air surrounding said consumer article. The container can be made of any material usable for this kind of consumer article. Naturally, said material must be chemically inert towards the composition of the invention. Standard packages used for these kinds of articles, such as plastics-polypropylene, polyvinyl chloride, high density polyethylene, P.E.T. and glass, are well suited.

During storage, at least the portion of the container that is able to allow the release of the vapors into the exterior of said contained is sealed, in order not to allow diffusion of the volatile liquid phase into the surroundings. The consumer will then activate the consumer article simply by removing the seal, after which the volatile liquid phase will start to diffuse into the surrounding air.

Such a volatile material dispenser can be, depending on the nature of the active volatile used in the preparation of the gel a perfuming or sanitizing device. Non-limiting examples of said volatile material dispenser as an air-freshener, particularly of the solid type, are a diaper pail freshener, a car freshener, a closet freshener, a wardrobe air-freshener, a drawer freshener, an animal litter box freshener, a shoe freshener or a garbage pail freshener, an insecticide or an insect repellent device, or a mothproofer.

In fact, a container and an adequate gel composition of the invention will compose said consumer article. The gel can be housed in the container or a packaging material.

The invention also relates to a process for diffusing an active volatile ingredient into ambient air by exposing the gel device of the invention to air. In a preferred embodiment of the invention, the gel device is exposed to air in a closed space such as for example a room, a cupboard, a wardrobe, a drawer, an animal litter box or a garbage container. Therefore, another object of the present invention is a method to modulate, enhance or modify the evaporation of an active volatile ingredient comprising the step of providing a gel composition as defined above.

Another object of the present invention is the use of the gel composition as defined above as an air freshener.

The invention will now be described in further detail by way of the following examples wherein the amounts are indicated in % by weight, relative to the weight of the gel composition, and the temperatures are indicated in degrees centigrade.

Example 1

Preparation of a Gel Composition (Gel 1) According to the Invention

A gelling agent comprising cellulose, hemicellulose and pectin (FiberGel®, trademark from Florida Food Products, Inc. and commercially available from Florida Food Products, Inc.) (34.2 g, 2.9 wt %) was added to water (1132.9 g, 94.4 wt %) while stirring (10-15 minutes). Sodium tripolyphosphate (2.4 g, 0.2 wt %) was added and the mixture was heated to 80° C. Then Calcium Phosphate (2.4 g, 0.2 wt %) and Glucono-Delta-Lactone (14.9 g, 1.2 wt %) were added. Then, a perfume oil (Table 1 or Table 2, 12 g, 1.0 wt %) and an antimicrobial/preservative (NEOLONE™, trademark from The Dow Chemical Company, 1.2 g, 0.1 w %) were added and mixed in. The resulting mixture was poured into several suitable molds and allowed to cool. The thermal stability of the obtained gel has been assessed with a Kofler Bench showing that such hydrogel could be heated up to 100° C. without melting or substantial change in gel structure.

TABLE 1

Perfume composition of floral, marine, ozonic, fruity type

| Raw material | % |
|---|---|
| Benzyl acetate | 2.50 |
| Hexyl acetate | 5.40 |
| Prenyl acetate | 0.40 |
| Aldehyde C10 | 1.60 |
| Allyl amyl glycolate | 0.50 |
| Undecalactone gamma | 1.50 |
| Calone ®[1)] | 0.15 |
| Ethyl caproate | 0.30 |
| Cetalox ®[2)] | 0.15 |
| Citronellol | 2.20 |
| Verdyl acetate[3)] | 1.00 |
| Delta damascone | 0.10 |
| Dihydromyrcenol | 7.00 |
| Dipropylene glycol | 35.00 |
| 4-(1,1-diméthyléthyl)-1-cyclohexyl acetate[5)] | 3.30 |
| Eugenol | 0.50 |
| Farenal[5)] | 0.30 |
| Floralozone[6)] | 1.00 |
| Iso e super[7)] | 1.60 |
| Isoraldeine[8)] | 0.50 |
| Lavandin grosso | 1.30 |
| Lilial ®[9)] | 4.00 |
| 2,6-diméthyl-5-heptanal[10)] | 1.00 |
| Menthone | 0.50 |
| Crystal moss | 0.30 |
| Ethyl 2 methylbutyrate | 2.20 |
| Neobutenone ®[11)] alpha | 0.10 |
| Ethyl oenanthate | 1.10 |
| Phenylethyl alcohol | 2.20 |
| Precyclemone b[12)] | 0.60 |
| Rosemary oil | 0.60 |
| Hexyl salicylate | 4.40 |
| (Z)-3-hexenyl 2-hydroxybenzoate | 1.10 |
| Scentenal ®[13)] | 0.60 |
| Mixture of terpenes from orange | 5.50 |
| Verdox ™[14)] | 6.60 |
| Beta ionone | 2.00 |
| 2,4-Dimethyl-3-cyclohexene-1-carbaldehyde[165)] | 0.90 |

[1)]7-Methyl-2H,4H-1,5-benzodioxepin-3-one; origin: Firmenich SA, Geneva, Switzerland
[2)]dodecahydro-3a,6,6,9a-tetramethyl-naphtho[2,1-b]furan; origin: Firmenich SA, Geneva, Switzerland
[3)]mixture of tricyclo[5.2.1.0(2,6)]dec-3-en-8-yl acetate and tricyclo[5.2.1.0(2,6)]dec-4-en-8-yl acetate
[4)]origin: Firmenich SA, Geneva, Switzerland
[5)]2,6,10-trimethyl-9-undecenal; origin: Symrise AG, Germany
[6)]3-(4/2-Ethylphenyl)-2,2-dimethylpropanal; origin: International Flavors & Fragrances, USA
[7)]1-(octahydro-2,3,8,8-tetramethyl-2-naphtalenyl)-1-ethanone; origin: International Flavors & Fragrances, USA
[8)]N-methyl ionone; origin: International Flavors & Fragrances, USA
[9)]3-(4-tert-butylphenyl)-2-methylpropanal; origin: Givaudan-Roure SA, Vernier, Suisse
[10)]Origin: Givaudan-Roure SA, Vernier, Suisse
[11)]1-(5,5-dimethyl-1-cyclohexen-1-yl)-4-penten-1-one; origin: Firmenich SA, Geneva, Switzerland
[12)](+−)-1-methyl-4-(4-methyl-3-pentenyl)-3-cyclohexene-1-carbaldehyde; origin: International Flavors & Fragrances, USA
[13)]8(9)-méthoxy-tricyclo[5.2.1.0.(2,6)]décane-3(4)-carbaldehyde; origin: Firmenich SA, Geneva, Switzerland
[14)]2-tert-butyl-1-cyclohexyl acetate; origin: International Flavors & Fragrances, USA
[15)]origin: Firmenich SA, Geneva, Switzerland

TABLE 2

Perfume composition of floral, white floral type

| Raw material | wt % |
|---|---|
| Benzyl acetate | 10.0 |
| Citronellol | 2.0 |
| Coranol[1)] | 5.0 |
| Decalactone gamma | 1.0 |
| Delta damascone | 0.1 |
| Dihydromyrcenol | 2.5 |
| Dipropylene glycol | 21.8 |
| Eugenol | 1.0 |
| Florol ®[2)] | 6.0 |
| Geranyl acetate | 1.5 |
| Hedione ®[3)] | 3.0 |
| Iso e super[4)] | 3.0 |
| Lilial ®[5)] | 2.0 |
| Linalol | 10.0 |
| Methyl anthranilate | 1.5 |
| Phenylacetaldehyde dimethyl acetal | 0.5 |
| Phenylethyl alcohol | 7.0 |
| (Z)-3-hexenyl 2-hydroxybenzoate | 1.0 |
| Styrallyl acetate | 2.0 |
| Undecalactone gamma | 2.5 |
| Verdox ™[6)] | 7.0 |
| Verdyl acetate[7)] | 5.0 |
| Verdyl propionate[8)] | 4.0 |
| 2,4-Dimethyl-3-cyclohexene-1-carbaldehyde[9)] | 0.6 |

[1)]4-cyclohexyl-2-methyl-2-butanol; origin: Firmenich SA, Geneva, Switzerland
[2)]tetrahydro-2-isobutyl-4-methyl-4(2H)-pyranol; origin: Firmenich SA, Geneva, Switzerland
3)Methyl dihydrojasmonate; origin: Firmenich SA, Geneva, Switzerland
[4)]1-(octahydro-2,3,8,8-tetramethyl-2-naphtalenyl)-1-ethanone; origin: International Flavors & Fragrances, USA
[5)]3-(4-tert-butylphenyl)-2-methylpropanal; origin: Givaudan-Roure SA, Vernier, Suisse
[6)]2-tert-butyl-1-cyclohexyl acetate; origin: International Flavors & Fragrances, USA
[7)]mixture of tricyclo[5.2.1.0(2,6)]dec-3-en-8-yl acetate and tricyclo[5.2.1.0(2,6)]dec-4-en-8-yl acetate
[8)]mixture of tricyclo[5.2.1.0(2,6)]dec-3-en-8-yl propanoate and tricyclo[5.2.1.0(2,6)]dec-4-en-8-yl propanoate (b)
[9)]origin: Firmenich SA, Geneva, Switzerland Example 2

Preparation of a Gel Composition According to the Invention

A gelling agent comprising cellulose, hemicellulose and pectin (Citri-Fi®, trademark from FiberStar® and commercially available from FiberStar®) (7.5 g, 3 wt %) was added to water (224.7 g, 89.8 wt %) while stirring (10-15 minutes). Sodium tripolyphosphate (1.3 g, 0.5 wt %) was added and the mixture was heated to 80° C. Then Calcium Phosphate dibasic (1.0 g, 0.4 wt %) was added. Then, a perfume oil (Table 2, 12.5 g, 5 wt %) and Glucono-Delta-Lactone (3.1 g, 1.2 wt %) were added and mixed in. The resulting mixture was poured into suitable molds and allowed to cool.

The thermal stability of the obtained gel has been assessed with a Kofler Bench showing that such hydrogel could be heated up to 100° C. without melting or substantial change in gel structure.

Example 3

Preparation of Gel Composition (Gels A to E) According to the Invention

Gels according to the invention (Gel A to E) were prepared following the procedure described in example 1 with the following ingredients:

TABLE 3

Composition of Gel A to E

| Ingredient | Gel A Amount (wt %) | Gel B Amount (wt %) | Gel C Amount (wt %) | Gel D Amount (wt %) | Gel E Amount (wt %) |
|---|---|---|---|---|---|
| Water | 87.16 | 95.40 | 94.74 | 94.92 | 95.14 |
| Gelling agent[1] | 2.58 | 2.35 | 2.50 | 2.34 | 2.35 |
| Sodium tripolyphosphate | 0.18 | 0.20 | 0.20 | 0.20 | 0.20 |
| Calcium Phosphate | 0.18 | 0.20 | 0.20 | 0.20 | 0.20 |
| Glucono-Delta-Lactone | 1.12 | 1.24 | 1.24 | 1.23 | 1.24 |
| Preservative[2] | 0.09 | 0.10 | 0.10 | 0.11 | 0.10 |
| polyethylene glycol 1000 [3], dibutyl lauroyl glutamide and dibutyl ethylhexanoyl glutamide[4] | 8.69 | 0 | 0 | 0 | 0 |
| Locust Bean Gum | 0 | 0.51 | 0 | 0 | 0.50 |
| Cetyl Alcohol | 0 | 0 | 1.03 | 0 | 0 |
| Guar Gum | 0 | 0 | 0 | 1.00 | 0 |
| Carboxy Methyl Cellulose | 0 | 0 | 0 | 0 | 0.25 |

[1] FiberGel ®, trademark from Florida Food Products, Inc. and commercially available from Florida Food Products, Inc.
[2] Neolone ™, trademark from The Dow Chemical Company
[3] Carbowax ®; trademark from The Dow Chemical Company
[4] The mixture consist of 96 wt % of polyethylene glycol 1000, 2 wt % of dibutyl lauroyl glutamide and 2 wt % dibutyl ethylhexanoyl glutamide; the mixture was added after Glucono-Delta-Lactone
Locust Bean Gum, Guar Gum and Carboxy Methyl Celluloseare added to the aqueous solution of gelling agent, whereas Cetyl Alcohol is added before the addition of Calcium Phosphate.

Example 4

Preparation of a Control gel composition (Gel 2) based on carrageenan

A carrageenan powder consisting primarily of kappa-carrageenans (34.2 g, 2.85 w %) was slowly added to water (1152.6 g, 96.05 w %) at 80° C. The solution was stirred until a uniform liquid was obtained. After ~10 minutes of stirring, a perfume oil (Table 1 or Table 2, 12 g, 1 w %) and an antimicrobial/preservative (NEOLONE™ 1.2 g, 0.1 w %) were added. The resulting mixture was poured into several suitable molds and allowed to cool to room temperature.

Example 5

Fragrance Release Over Time of a Gel Composition According to the Invention Compared with a Control Gel Composition Hydrogels prepared as reported in examples 1 and 4 (Gel 1 and Gel 2) with the perfume of Table 1 were molded in commercial cone shape. Samples obtained were dried over 4 weeks at constant temperature (20° C.), and relatively constant % relative humidity (~60% relative humidity). At certain intervals (weekly) the cones were placed in closed desiccators for 2 hours, and the headspace was collected for 30 minutes using a SPME fiber (SUPELCO 85 μm Polyacrylate SPME fiber). The SPME fiber was desorbed in a GC injector at 250° C. for 2 minutes, splitless injection. The analysis was performed using an Agilent GCMS (6890GC, 5973 MSD) equipped with a DB-WAXetr column (30 m×0.320 mm, 0.25 μm film). The peak areas from the MS detector for the compounds in the headspace were summed and averaged for triplicate samples. FIG. 1 reports the Average Sum of the GC-MS peak area of volatile compounds as a function of time and illustrates the fact that the hydrogel cone of the present invention shows fragrance release that is comparable to Gel 2, which is a reference in terms of fragrance release profile over time.

Example 6

Olfactive Performance of Gel Composition According to the Invention (Gel 1) Compared with Control Gel Composition (Gel 2)

A sensory test (n>30) was performed on 4 hydrogel cones according to the present invention having different concentrations of perfume (perfume composition of Table 2) and 4 control hydrogel cones with same concentrations of perfume (perfume composition of Table 2). The respective four cones differed in fragrance concentration ranging from 0% w/w, 0.23% w/w (corresponding to 25% of typical Commercial Fragrance Concentration; i.e. namely, 0.9% w/w), 0.45% w/w (corresponding to 50% of typical Commercial Fragrance Concentration; i.e. namely, 0.9% w/w) and 0.9% w/w (corresponding to 100% of typical Commercial Fragrance Concentration). The samples contained a dye to obscure any color differences. Panelists were asked to smell the opened air fresheners in the 'wet' state (time=0), by smelling the gel approximately 2.5 cm from their nose in a dedicated sensory booth.

Samples were evaluated by series of two (1 gel corresponding to the invention and 1 gel corresponding to control) and panelists, for each fragrance concentration, had to designate:
1) the gel with highest fragrance intensity;
2) overall preferred gel; and
3) gel with highest off-notes.

Results are indicated in table 4 with corresponding p-values.

TABLE 4

Sensory results

| Fragrance concentration | Fragrance intensity | Preference | Off-notes |
|---|---|---|---|
| 0% of CFC | NA | Gel 1<br>$P < 0.001$ | Gel 2<br>$P < 0.001$ |
| 25% of CFC | Gel 1<br>$P = 0.0410$ | Gel 1<br>$P < 0.01$ | Gel 2<br>$P < 0.001$ |
| 50% of CFC | Gel 1<br>$P = 0.0167$ | Gel 1<br>$P < 0.001$ | Gel 2<br>$P < 0.001$ |
| 100% of CFC | Gel 1<br>$P = 0.0895$ | Gel 1<br>$P < 0.001$ | Gel 2<br>$P < 0.001$ |

Sensory data show that the perceived fragrance intensity from air fresheners with any fragrance levels was higher for those made with Gel 1 than those made with the control Gel 2. Even at 100% fragrance level, substantially more panelists rated Gel 1 of the present invention as more intense (23 out of 35

On the other hand, the preference for Gel 1 of the present invention was highly significant at all fragrance levels. Finally, off note intensity was significantly stronger for the control Gel 2 at all levels as well. Common descriptors for the perceived off notes were "Fishy", "Marine" and "Swampy".

The invention claimed is:
1. A gel composition comprising:
   a) a gelling agent comprising cellulose, hemicellulose and pectin, in an amount comprised between 0.1% and 10% by weight, relative to the total weight of the composition;

b) an active volatile ingredient-containing oil in an amount comprised between 0.1 and 5% by weight, relative to the total weight of the composition;
c) water in an amount comprised between 85% and 98.9% by weight, relative to the total weight of the composition;
d) a bivalent cation, in an amount comprised between 0.01% and 1% by weight, relative to the total weight of the composition;
e) a sequestering agent, in an amount below 0.5% by weight, relative to the total weight of the gel composition; and
f) a pH modifier, in an amount below 3% by weight, relative to the total weight of the gel composition;

wherein the composition is an air freshener, and
wherein the gelling agent is devoid of chemically modified cellulose.

2. The gel composition according to claim 1, wherein the active volatile ingredient is a perfume.

3. The gel composition according to claim 1, wherein the bivalent cation is calcium phosphate.

4. The gel composition according to claim 1, wherein the pH modifier is glucono delta lactone.

5. The gel composition according to claim 1, wherein the sequestering agent is sodium tripolyphosphate.

6. A process for the preparation of a gel composition according to claim 1 comprising the following steps:
   a) mixing a gelling agent comprising cellulose, hemicellulose and pectin with water;
   b) adding to the mixture obtained in step a), a sequestering agent;
   c) optionally heating the mixture obtained in step b);
   d) adding to the mixture obtained in step c):
      i) a bivalent cation;
      ii) a pH modifier; and
      iii) an active volatile ingredient containing-oil.

7. The process according to claim 6, wherein the gel is further poured into a mold or suitable container before being allowed to cool down to room temperature.

8. The process according to claim 6, wherein the pH modifier is Glucono delta lactone.

9. The process according to claim 6, wherein the pH modifier is added in amount comprised between 0.01% to 3% by weight, relative to the total weight of the gel composition.

10. A method to modulate, enhance or modify the evaporation of an active volatile ingredient comprising the step of providing the gel composition according to claim 1.

11. A method for freshening the air comprising dispensing from an air freshener the gel according to claim 1.

* * * * *